United States Patent [19]

Terayama

[11] Patent Number: 4,896,986
[45] Date of Patent: Jan. 30, 1990

[54] ENDOSCOPE CONNECTING APPARATUS

[75] Inventor: Toshiki Terayama, Kogenei, Japan

[73] Assignee: Olympus Optical Co, Ltd., Tokyo, Japan

[21] Appl. No.: 104,891

[22] Filed: Oct. 6, 1987

[30] Foreign Application Priority Data

Oct. 8, 1986 [JP] Japan .................. 61-240300

[51] Int. Cl.⁴ .............................................. B25G 3/00
[52] U.S. Cl. ...................................... 403/14; 403/325; 403/322; 128/4
[58] Field of Search ................. 403/327, 325, 322, 14; 128/4

[56] References Cited

U.S. PATENT DOCUMENTS

| | | | |
|---|---|---|---|
| 1,880,551 | 10/1932 | Wappler | 128/7 |
| 2,584,619 | 2/1952 | Rubens et al. | 128/5 |
| 3,362,050 | 1/1968 | McCarthy | 403/325 |
| 4,452,546 | 6/1984 | Hiltebrandt et al. | 403/327 |
| 4,550,715 | 11/1985 | Santangelo et al. | 128/4 |
| 4,697,946 | 10/1987 | Rock et al. | 403/327 |
| 4,723,864 | 2/1988 | Umeda et al. | 403/322 |

*Primary Examiner*—Andrew V. Kundrat
*Attorney, Agent, or Firm*—Armstrong, Nikaido, Marmelstein, Kubovcik & Murray

[57] ABSTRACT

A connecting mechanism is formed by providing grooves having angularly disposed slopes in a rotary member in a position facing the outside of guide grooves provided in a housing for engaging endoscope fitting pins and providing an energizing device biasing the rotary member for rotation in one direction so that the endoscope may be locked and fitted by the simple operation of pushing in the endoscope forward through an open end of the housing.

8 Claims, 3 Drawing Sheets

ENDOSCOPE CONNECTING APPARATUS

BACKGROUND OF THE INVENTION

Field of the Invention and Related Art Statement

This invention relates to an endoscope connecting apparatus whereby an endoscope can be easily fitted by rotation of a rotary member which is effected by inserting the endoscope forward through an open end of the housing.

Recently, there has come to be extensively used an endoscope whereby a body cavity can be observed or treated with a treating tool without requiring any incision by inserting an elongated insertable part.

Among the above mentioned endoscopes, there are a rigid endoscope wherein the insertable part is rigid and a flexible endoscope wherein the insertable part is flexible. In the case of using such rigid endoscope, it is used generally as connected to such endoscope connecting apparatus as a hollow trocar outer needle.

As the first prior art example of the above mentioned endoscope connecting apparatus, there is one disclosed in U.S. Pat. No. 4452546. In this prior art example, in connecting the endoscope, there are required operations of pushing the scope forward while rotating it with respect to an outer needle. As these two operations are required, the operation is complicated and effective operability has not been high.

In the second prior art example shown in FIG. 1, a sliding ring 3 energized upward by a spring 2 is provided on the outer periphery of a (connecting apparatus) body 1 having an end opening. A groove 5 provided with two slopes 4a and 4b angularly disposed relative to each other is formed on the inner peripheral surface of this sliding ring 3. When a pin provided in the connecting part of the scope is inserted, one slope 4a will be pushed against the energizing force of the above mentioned spring 2 to move the sliding ring 3 downward to the opening position. Then, when the pin passes over the above mentioned slope 4a, the other slope 4b will push the pin forward with the energizing force of the spring 2 so that the sliding ring 3 will fix the scope with respect to the outer needle. In this second prior art example, the fitting operation may be effected with one movement. However, as the sliding ring 3 moves vertically, it will be large.

In the above mentioned second prior art example, there has been a defect that, though the operation is simple, in the case of replacing the endoscope with which a body cavity as filled with water is to be observed, even if the opening of the connecting part is pressed with a finger to prevent water from leaking out, the sliding ring will be so large as to be unable to be covered and water will be likely to leak out. There has been also a disadvantage that the structure is so difficult to be positively sealed against the movement of the sliding ring 3 that water is likely to leak out through the clearance between the sliding ring 3 and body 1.

OBJECTS AND SUMMARY OF THE INVENTION

An object of the present invention is to provide an endoscope connecting apparatus whereby an endoscope can be fitted by a simple operation.

Another object of the present invention is to provide an endoscope connecting apparatus which is high in such operability as the capability of locking an endoscope when it is fitted.

Further, another object of the present invention is to provide an endoscope connecting apparatus which can prevent water from leaking out.

In the present invention, a connecting mechanism having a cylindrical housing part is provided with guide grooves for receiving engaging projections provided on the endoscope, grooves having a wall part defined by sloped walls oriented at an angle to each other are provided in a rotary ring rotatably fitted to a base end part of the body of the connecting apparatus and an energizing means is provided for energizing the rotary ring in one direction so that the above mentioned slopes may close the grooves is formed in the housing part which is provided with an opening for receiving an endoscope insertable part in the base end part of the connecting apparatus body so that, by the operation of pushing in the endoscope, the rotary ring may be rotated against the energization of the above mentioned energizing means to engage the projections of the above mentioned endoscope and then the rotary ring is rotated in the reverse direction by the above mentioned energizing means to automatically lock the endoscope that is pushed in.

BRIEF DESCRIPTION OF THE DRAWINGS

FIG. 3 is a sectioned view showing a first embodiment of an endoscope connecting apparatus of the present invention.

FIG. 4 is an end view of the apparatus of FIG. 1.

FIG. 5 is a sectioned view on line A—A' in FIG. 1.

FIG. 6 is a perspective view showing an endoscope adapted to be fitted to the apparatus of the first embodiment.

FIG. 7 is a sectioned view on line B—B' in FIG. 1.

FIG. 8 is a perspective view showing the shapes of grooves provided in the rotary ring.

FIG. 9 is an explanatory view showing how pins of an endoscope are engaged by pushing the slopes of the rotary ring as an endoscope is inserted.

DETAILED DESCRIPTION OF PREFERRED EMBODIMENTS

Figure 3:
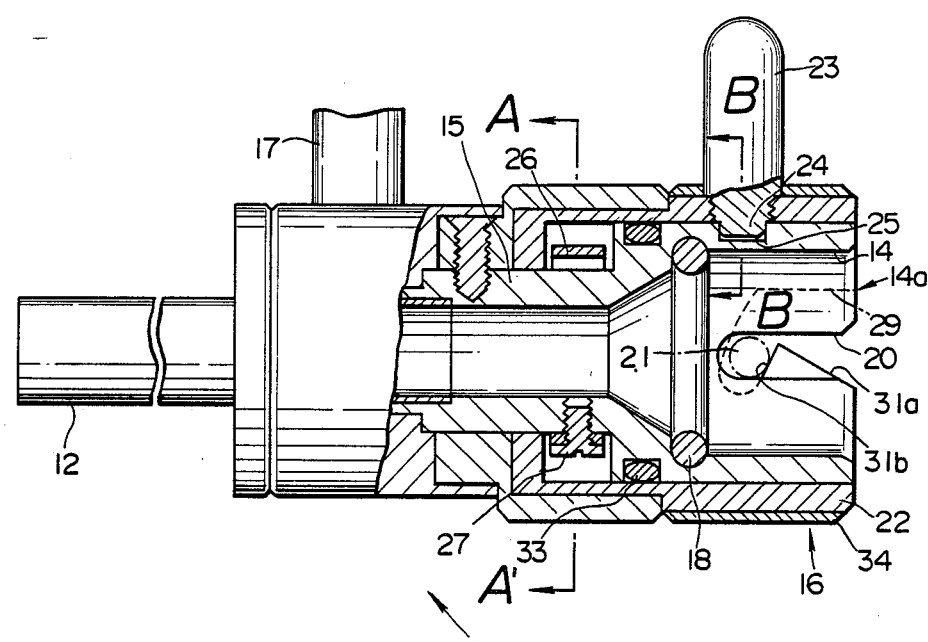
Figure 6:
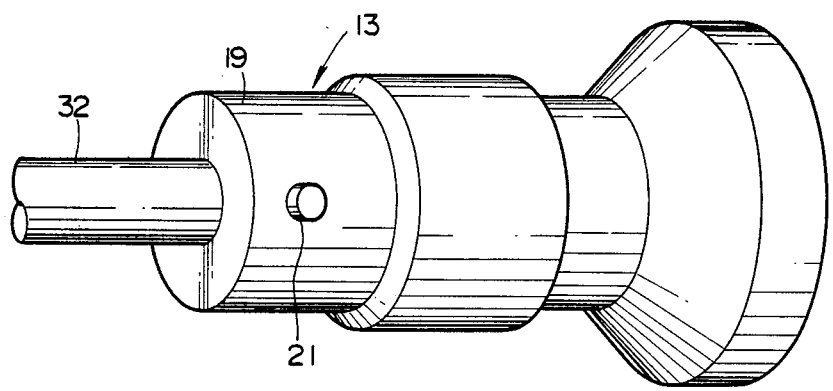

With reference to FIG. 3, there is shown an endoscope connecting apparatus 11 of the first embodiment which comprises an elongated hollow sleeve 12, a (connecting apparatus) body 15 connected to the rear of this sleeve 12 and provided in the base end part with a housing part 14 having an opening 14a through which an endoscope (scope) 13 shown in FIG. 6 can be inserted from the rear and a connecting mechanism (mounting mechanism) 16 formed on the base end side of this body 15.

In the outer peripheral part on the front part side of the body 15 in the part in which the above mentioned sleeve 12 is secured, a ring-like member and a projecting water feeding mouthpiece 17 are provided. The inside diameter of this body 15 is expanded as it tapers rearward and, a ring-like recess is provided internally at the inner end of the inner wall surface of the housing part 14 to receive a water-sealing O-ring 18. In case the scope 13 is fitted within the housing part 14, this O-ring 18 will be pressed by the front end surface of a connecting part 19 of the scope to prevent water leakage from the forward part of the connecting apparatus.

The above mentioned connecting mechanism 16 is of such structure as in the following.

Figure 1:
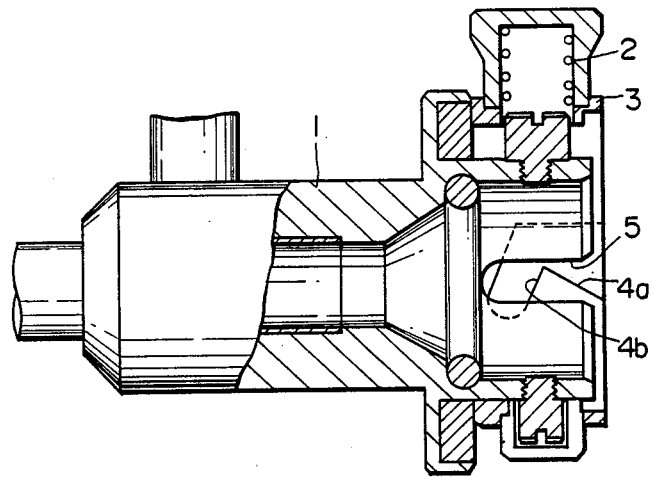
FIG. 1 is a sectioned view showing an endoscope connecting apparatus of a prior art example.
Figure 2:
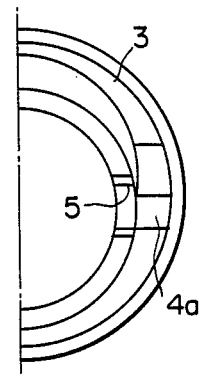
FIG. 2 is a partial end view of the apparatus of FIG. 1.
Figure 4:
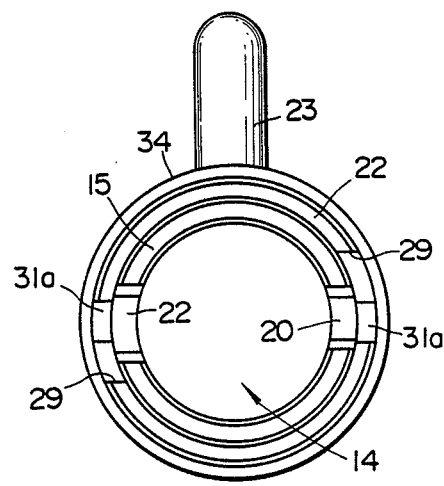
FIGS. 3 to 9 relate to the first embodiment of the present invention.

On the wall surface of the housing part 14 of the above mentioned body 15, two guide grooves 20 (See FIG. 4) are angularly spaced 180 degrees from each other and extend toward the front part (deep part) from the opening end so as to be able to house pins 21 (only one is shown in FIG. 6) provided to project on a connecting part 19 of the scope 13.

Figure 5:
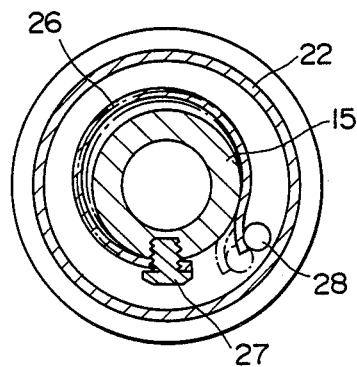
Figure 7:
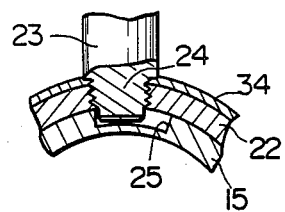
Figure 8:
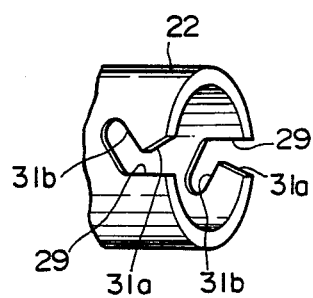
Figure 9:
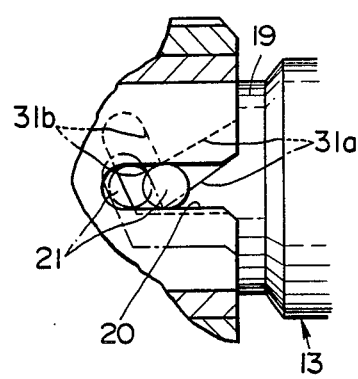

A rotary ring 22 is rotatably fitted to the cylindrical outer periphery of the rear part of the above mentioned body 15 and is provided with a projecting knob 23 screwed in the ring 22. A pin 24 at the tip of the base of this knob 23 passes through the rotary ring 22, projects in the body 15 inside the rotary ring 22 and is received within an arcuate groove 25 in the peripheral direction of this body 15. A spring 26 formed by arcuately bending a spring plate is housed in a space or peripheral groove formed between the front inner periphery of the above mentioned rotary ring 22 and the outer periphery of the body 15. As shown in FIG. 5, this spring 26 is secured at one end to the body 15 by a screw 27 and is seated at the other end against a pin 28 attached to and projecting from an internal surface of the rotary ring 22. By this spring 26, the rotary ring 22 is energized or biased in a counter-clockwise direction. If the rotary ring 22 is rotated against this energization, the spring 26 will be of a small radius of curvature as shown by the one-point chain line from the state shown by the solid line in FIG. 5. By the above mentioned spring 26, the pin 24 in the base part of the above mentioned knob 23 is positioned as pressed against one groove wall surface within the arcuate groove 25 as shown in FIG. 7. The rotary ring 22 is provided with grooves 29 radially outward and opposing the guide grooves 20 of this body 15. The above mentioned grooves 29 coincide in the deep part with the inside guide grooves 20 due to the energizing force of the above mentioned spring 26. As shown in FIG. 8, two slopes 31a and 31b each of which projects toward the other side part so as to reduce the width of the groove 29 are provided each on one side part (groove wall part) of the respective grooves 29. These two slopes 31a and 31b are angularly disposed to slope in the directions reverse to each other and project so as to reduce (close) the groove width from the inlet side to the central part of the inside guide groove 20. Therefore, when the scope 13 is inserted into the opening 14 from the elongated insertable part 32 side, each pin 21 of the scope 13 will be in contact with the above mentioned slope 31a. If the above mentioned slope 31a is pushed against the energizing force of the spring 26, the rotary ring 22 will rotate and the pins 21 will be able to be pushed into the deep part sides of the grooves 20 and 29 over the slopes 31a. This manner is shown by the solid lines in FIG. 9. When the pins 21 pass over the slopes 31a as thus pushed in, the rotary ring 22 will rotate counter-clockwise. In such case, the pins 21 will slide on the other slopes 31b and will be housed in the deepest parts of both guide grooves 20 and 29. This state is shown by the one-point chain line in FIG. 9. In this state, the pins 21 will contact the steep slopes 31b and will be held as locked to be prevented from being pulled out rearward.

On the outer peripheral surface of the body 15 in the fitting part with the inside diameter of the above mentioned rotary ring 22 as its outside diameter, a ring-like recess is provided to fit a water-sealing O-ring 33 which is to prevent water from leaking out of the fitting part of the body 15 and rotary ring 22. By the way, the rotary ring 22 is covered on the outer peripheral surface with a cover 34 to prevent water from leaking out of the guide grooves 20 and 29.

By the way, one of two guide grooves 20 provided on the wall surface of the housing part 14 of the body 15 is made larger to prevent the scope 13 from being fitted as reversely directed. (In FIG. 4, the left side guide groove 20 is larger than the other.) The two pins 21 provided on the scope 31 side are also formed to be of different diameters with the diameter of each pin sized to fit one of the grooves 20.

The operation of removably fitting the scope 13 by the thus formed first embodiment shall be explained in the following manner.

First of all, a trocar inner needle, not illustrated, is fitted through the opening 14a of the connecting apparatus 11 of the first embodiment and is thrust into an abdomen hole. When this inner needle is pulled out and the insertable part 32 side of the scope 13 is inserted into the housing part 14, the insertable part 32 of the scope 13 will be inserted into the sleeve 12 of the connecting apparatus 11 and the respective pins 21 of the connecting part 19 of the scope 13 will contact the slopes 31a of the rotary ring 22 in the inlet parts of the guide grooves 20 and 29. If the scope 13 is pushed out forward from this state, the slopes 31a will be pushed and the rotary ring 22 will rotate against the energizing force of the spring 26. The guide grooves 20 previously closed by the slopes 31a will be opened by this rotation to be in an opened state capable of receiving and housing the pins 21. As shown by the solid lines in FIG. 9, the pins 21 will move further in the guide grooves 20. When the pins 21 enter the guide grooves 20 until they are positioned over the tops of the slopes 31a (substantially the position indicated by the solid lines in FIG. 9), by the energizing force of the spring 26, the rotary ring 22 will be rotated in the reverse direction (reverse to the direction moved by the pins pushing the above mentioned slopes 31a). By this rotation, the pins 21 will slide on the steep slopes 31b, until they reach the deepest parts of the grooves 20 and will be prevented by the steep slopes 31b from being pulled out, that is, will be locked and fitted in place. In this state, the peripheral edge of the radial front end surface of the connecting part 19, provided in the form of a step in the scope 13, will press the O-ring 18 to prevent water leakage through the opening 14a.

By the way, prior to inserting the above mentioned scope 13, water will be prevented from leaking out of this opening 14a.

On the other hand, in the case of removing the fitted scope 13, if the knob 23 is rotated clockwise against the energizing force of the spring 26, the slopes 31b locking the pins 21 on the rear side of the pins 21 will rotate and retreat together with the rotary ring 22 and will unlock the pins 21 so that the scope 13 will be able to be simply pulled out.

According to this first embodiment, in fitting the scope 13, by the simple operation of inserting and merely pushing the insertable part 32, the scope 13 can be automatically fitted.

In removably fitting the scope, the rotating rotary ring 22 is a substantially cylindrical ring externally fitting the body 15 and the water leakage can be simply prevented by the O-ring 33. In replacing the scope 13, by pressing the opening 14a with a thumb, water leakage can also be prevented.

Figure 10:
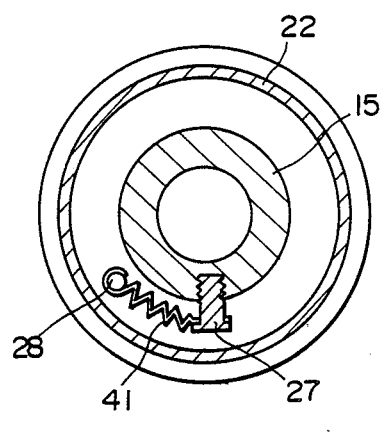
FIG. 10 is a sectioned view showing a rotary ring energizing means in the second embodiment of the present invention.

FIG. 10 shows an energizing means of the rotary ring 22 in the second embodiment of the present invention.

In this second embodiment, a cylindrical coil spring 41 is used in place of the spring 26 in the first embodiment. This coil spring 41 energizes the rotary ring 22 counter-clockwise. Therefore, when the scope 13 is pushed in, the rotary ring 22 will rotate clockwise to compress this coil spring.

The operation and effect of this second embodiment are the same as of the above mentioned first embodiment.

Figure 11:
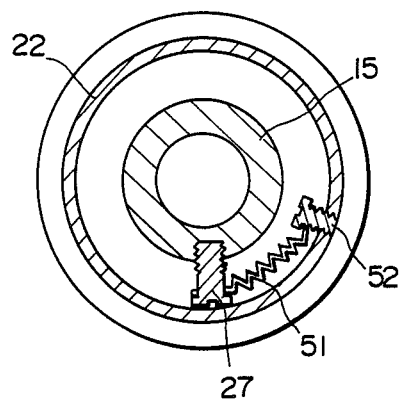
FIG. 11 is a sectioned view showing a rotary ring energizing means in the third embodiment of the present invention.

FIG. 11 shows an energizing means of the rotary ring 22 in the third embodiment of the present invention.

In this third embodiment, the same as in the above mentioned second embodiment, a coil spring 51 is used to energize the rotary ring 22 counter-clockwise. By the way, in this case, the coil spring 51 is fixed at one end to the rotary ring 22 by a screw 52. Therefore, when the scope 13 is pushed in, the rotary ring 22 will rotate clockwise to extend this coil spring 51. The operation and effect of this third embodiment are the same as of the above mentioned second embodiment.

By the way, in the above mentioned first embodiment, two peripheral grooves 29 are provided in the rotary ring 22 and are provided with the slopes 31a and 31b. However, three or more grooves or one groove may be provided. Also, the two guide grooves 20 of the body 15 may have the same width.

As described above, according to the present invention, there is provided a fitting mechanism wherein, in the operation of inserting and pushing in a scope, a rotary member provided with grooves so that slopes may be pressed and projections of the scope may be engaged with the grooves is rotated and then is rotated in the reverse direction so as to be locked and therefore the scope can be fitted by a simple operation.

What is claimed is:

1. An endoscope connecting apparatus comprising:
a body part including a cylindrical housing part open at one end of said body part and adapted for housing a large diameter connecting part formed at the rear end of an insertable part of an endoscope, two fitting pins projecting from the outer periphery of said large diameter connecting part and a pair of guide grooves formed on the wall surface of said cylindrical housing part open at said one end of said body part with each guide groove adapted to engage one of said fitting pins;
a rotary ring rotatably fitted to a cylindrical outer peripheral surface of said cylindrical housing part;
a pair of groove parts formed in the part of said rotary ring facing the outside of each said guide groove, each of said groove parts including a first sloped groove wall forming an angle less than 90 degrees with the lengthwise direction of said guide groove and open at said one end of said body part and a second sloped groove wall connected to an end of said first sloped groove wall opposite from said open end and forming an angle less than 90 degrees with the lengthwise direction of said guide groove in a direction reverse to the slope of said first sloped groove wall, each said groove part having a width capable of housing one of said fitting pins; and
a rotary energizing means between opposed diametric surfaces of said body part and said rotary ring and biasing said rotary ring in one direction with respect to said body part so that said first and second sloped groove walls of each groove part close a part of respective ones of said guide grooves.

2. An apparatus according to claim 1 wherein said rotary energizing means comprises:
an arcuate plate spring housed in a peripheral groove formed between diametrical opposing surfaces of said body part and said rotary ring fitted to the outer peripheral surface of said body part; and
a fixing means fixing said plate spring at one end to said body part and at the other end to said rotary ring.

3. An apparatus according to claim 1 wherein said rotary energizing means is formed of a spring member housed within a peripheral groove formed between diametric opposing surfaces of said body part and said rotary ring and a fixing means fixing one end of said spring member to said body part and the other end of said spring member to said rotary ring.

4. An apparatus according to claim 1, wherein a peripheral groove is provided internally and at the inner end of the inner wall surface of said cylindrical housing part, said large diameter connecting part is bounded at one end by a sealing surface, and an O-ring is seated in said peripheral groove, so that said O-ring may contact the sealing surface of said large diameter connecting part and provide a waterproof seal when said fitting pin is engaged with the deepest part of said guide groove.

5. An apparatus according to claim 1 wherein said rotary ring is provided with a radially projecting releasing knob.

6. An apparatus according to claim 1 wherein each one of said fitting pins and said guide grooves is angularly positioned 180 degrees from the other one of said fitting pins and said guide grooves.

7. An endoscope connecting apparatus comprising:
a body part including a cylindrical housing part open at one end of said body part and adapted for housing a large diameter connecting part formed at the rear end of an insertable part of an endoscope, two fitting pins projecting from the outer periphery of said large diameter connecting part and a pair of guide grooves formed on the wall surface of said cylindrical housing part open at said one end of said body part with each guide groove adapted to engage one of said fitting pins;
one of said fitting pins having a diameter different from the diameter of the other fitting pin and the width of each of said guide grooves corresponding to the diameter of one of said fitting pins whereby said large diameter connecting part may only be connected when each fitting pin is aligned with a guide groove having a width corresponding to the diameter of said fitting pin;
a rotary ring rotatably fitted to a cylindrical outer peripheral surface of said cylindrical housing part;
a pair of groove parts formed in the part of said rotary ring facing the outside of each said guide groove, each of said groove parts including a first sloped groove wall forming an angle less than 90 degrees with the lengthwise direction of said guide groove and open at said one end of said body part and a second sloped groove wall connected to an end of said first sloped groove wall opposite from said open end and forming an angle less than 90 degrees with the lengthwise direction of said guide groove in a direction reverse to the slope of said first sloped groove wall, each said groove part having a width capable of housing one of said fitting pins; and a rotary energizing means biasing said rotary ring in one direction with respect to said body part so that said first and second sloped groove walls of each groove part close a part of respective ones of said guide grooves.

8. An endoscope connecting apparatus comprising:

a body part including a cylindrical housing part open at one end of said body part and adapted for housing a large diameter connecting part formed at the rear end of an insertable part of an endoscope, two fitting pins projecting from the outer periphery of said large diameter connecting part and a pair of guide grooves formed on the wall surface of said cylindrical housing part open at said one end of said body part with each guide groove adapted to engage one of said fitting pins;

a rotary ring rotatably fitted to a cylindrical outer peripheral surface of said cylindrical housing part;

a pair of groove parts formed in the part of said rotary ring facing the outside of each said guide groove, each of said groove parts including a first sloped groove wall forming an angle less than 90 degrees with the lengthwise direction of said guide groove and open at said one end of said body part and a second sloped groove wall connected to an end of said first sloped groove wall opposite from said open end and forming an angle less than 90 degrees with the lengthwise direction of said guide groove in a direction reverse to the slope of said first sloped groove wall, each said groove part having a width capable of housing one of said fitting pins and said second sloped groove wall of each groove part forming a larger angle with the lengthwise direction of an adjacent one of said guide grooves than the angle formed by said first sloped groove wall and the lengthwise direction of said guide groove; and a rotary energizing means biasing said rotary ring in one direction with respect to said body part so that said first and second sloped groove walls of each groove part close a part of respective ones of said guide grooves.

* * * * *